US012746019B2

(12) United States Patent
Hoye et al.

(10) Patent No.: US 12,746,019 B2
(45) Date of Patent: Sep. 29, 2026

(54) ULTRASONIC HYPOTUBE DEVICES FOR TREATMENT OF CTOS AND STENOTIC LESIONS

(71) Applicant: Bard Peripheral Vascular, Inc., Franklin Lakes, NJ (US)

(72) Inventors: Jessica Hoye, Phoenix, AZ (US); Nir Herlinger, Scottsdale, AZ (US); Peng Zheng, Chandler, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 105 days.

(21) Appl. No.: 18/682,163

(22) PCT Filed: Sep. 28, 2021

(86) PCT No.: PCT/US2021/052316

§ 371 (c)(1),
(2) Date: Feb. 8, 2024

(87) PCT Pub. No.: WO2023/055339

PCT Pub. Date: Apr. 6, 2023

(65) Prior Publication Data

US 2024/0374269 A1 Nov. 14, 2024

(51) Int. Cl.
*A61B 17/22* (2006.01)
*A61B 17/00* (2006.01)

(52) U.S. Cl.
CPC .. *A61B 17/22012* (2013.01); *A61B 17/00234* (2013.01); *A61B 2017/00199* (2013.01);
(Continued)

(58) Field of Classification Search
CPC ........ A61B 17/22012; A61B 17/00234; A61B 2017/00199; A61B 2017/00238;
(Continued)

(56) References Cited

U.S. PATENT DOCUMENTS 4,870,953 A 10/1989 Donmicheal et al.
4,898,575 A 2/1990 Fischell et al.
(Continued)

OTHER PUBLICATIONS

International Search Report and Written Opinion dated May 30, 2022, in International Application No. PCT/US2021/052316, pp. 1-13.

*Primary Examiner* — Andrew Restaino
(74) *Attorney, Agent, or Firm* — Dinsmore & Shohl LLP

(57) ABSTRACT

A catheter assembly includes an outer sheath and a hypotube ultrasonic transmission member. The outer sheath has a first end, a second end, a frustoconical side wall portion located proximal to the second end, and a sheath lumen extending from the first end to the second end. The hypotube ultrasonic transmission member is disposed in the sheath lumen. The hypotube ultrasonic transmission member has a hypotube side wall, a proximal hypotube portion, a distal hypotube portion, and a tapered intermediate portion. The proximal hypotube portion is configured to be operatively coupled to an ultrasonic transducer. The proximal hypotube portion has a first diameter, and the distal hypotube portion has a second diameter that is less than the first diameter. The tapered intermediate portion is configured to transition from the first diameter to the second diameter. The tapered intermediate portion is located proximate the frustoconical side wall portion.

18 Claims, 9 Drawing Sheets

(52) U.S. Cl.
CPC ............... *A61B 2017/00238* (2013.01); *A61B 2017/00305* (2013.01); *A61B 2017/00398* (2013.01); *A61B 2017/00477* (2013.01); *A61B 2017/00853* (2013.01); *A61B 2017/00876* (2013.01); *A61B 2017/22008* (2013.01); *A61B 2017/22015* (2013.01); *A61B 2017/22038* (2013.01); *A61B 2017/22079* (2013.01); *A61B 2217/005* (2013.01); *A61B 2217/007* (2013.01)

(58) Field of Classification Search
CPC .......... A61B 2017/00305; A61B 2017/00398; A61B 2017/00477; A61B 2017/00853; A61B 2017/00876; A61B 2017/22008; A61B 2017/22015; A61B 2017/22038; A61B 2017/22079; A61B 2217/005; A61B 2217/007; A61B 2017/00845; A61B 2017/22018; A61B 2017/22039; A61B 2017/22094; A61B 2017/320004; A61B 2017/320084
See application file for complete search history.

(56) References Cited

U.S. PATENT DOCUMENTS

| | | | | | |
|---|---|---|---|---|---|
| 5,163,433 | A * | 11/1992 | Kagawa | A61B 17/22012 | 604/27 |
| 5,188,102 | A * | 2/1993 | Idemoto | A61M 3/0279 | 606/45 |
| 5,207,648 | A | 5/1993 | Gross | | |
| 5,255,669 | A * | 10/1993 | Kubota | A61B 17/320068 | 601/3 |
| 5,344,395 | A | 9/1994 | Whalen et al. | | |
| 5,391,144 | A * | 2/1995 | Sakurai | A61B 18/1402 | 601/3 |
| 5,624,430 | A * | 4/1997 | Eton | A61M 25/0127 | 606/1 |
| 5,658,309 | A | 8/1997 | Berthiaume et al. | | |
| 5,673,707 | A | 10/1997 | Chandrasekaran | | |
| 5,706,827 | A * | 1/1998 | Ehr | A61M 25/09 | 600/585 |
| 5,782,797 | A | 7/1998 | Schweich, Jr. et al. | | |
| 5,895,378 | A | 4/1999 | Nita | | |
| 6,524,299 | B1 | 2/2003 | Tran et al. | | |
| 6,562,054 | B1 * | 5/2003 | Weber | A61B 17/320068 | 606/170 |
| 6,592,541 | B1 * | 7/2003 | Kurwa | A61F 9/00745 | 604/521 |
| 7,774,933 | B2 | 8/2010 | Wilson et al. | | |
| 8,361,057 | B2 | 1/2013 | Tanghoej et al. | | |
| 8,956,375 | B2 | 2/2015 | Nita et al. | | |
| 9,326,875 | B2 | 5/2016 | Shumer et al. | | |
| 9,387,308 | B2 | 7/2016 | Hinchliffe et al. | | |
| 9,913,962 | B2 | 3/2018 | Tal et al. | | |
| 2006/0116629 | A1 | 6/2006 | Tal et al. | | |
| 2006/0217664 | A1 | 9/2006 | Hattler et al. | | |
| 2008/0281228 | A1 | 11/2008 | Parodi et al. | | |
| 2012/0130233 | A1 * | 5/2012 | Nita | A61M 25/0068 | 601/2 |
| 2012/0239022 | A1 * | 9/2012 | Wolfe | A61M 25/0158 | 606/41 |
| 2013/0060169 | A1 * | 3/2013 | Yamada | A61B 17/22012 | 601/2 |
| 2013/0072824 | A1 | 3/2013 | Nita et al. | | |
| 2013/0082462 | A1 | 4/2013 | Young | | |
| 2013/0331872 | A1 * | 12/2013 | Parham | A61B 17/320068 | 606/169 |
| 2015/0025451 | A1 * | 1/2015 | Banko | A61M 1/774 | 604/35 |
| 2019/0143078 | A1 | 5/2019 | Tierney et al. | | |
| 2019/0216487 | A1 * | 7/2019 | Nita | A61B 17/320068 | |
| 2020/0094025 | A1 | 3/2020 | Wisman | | |
| 2020/0230359 | A1 | 7/2020 | Fojtik et al. | | |
| 2020/0276413 | A1 | 9/2020 | Katsurada et al. | | |
| 2021/0007760 | A1 | 1/2021 | Reisin | | |

* cited by examiner

ULTRASONIC HYPOTUBE DEVICES FOR TREATMENT OF CTOS AND STENOTIC LESIONS

CROSS-REFERENCE TO RELATED APPLICATIONS

This application is a U.S. National Phase of International Application No. PCT/US2021/052316, entitled "Ultrasonic Hypotube Devices for Treatment of CTOs and Stenotic Lesions" and filed September 28,2021, which is incorporated herein by reference in its entirety.

TECHNICAL FIELD

The present invention relates to the treatment of intravascular lesions, and, more particularly, to ultrasonic catheter systems and ultrasonic catheter assemblies for the treatment of chronic total occlusions and highly stenotic lesions within the peripheral vasculature.

BACKGROUND ART

Currently, ultrasound catheter devices provide disruption of blood vessel obstructions, such as vascular occlusions. Typically, an ultrasound catheter transmits vibrational energy from an ultrasonic transducer through a transducer horn and then a transmission member, such as a wire, to a distal head. The mechanical vibration of the catheter distal end ablates or disrupts the blood vessel obstruction, such as calcific occlusions.

What is needed in the art is longer, small profile devices for the treatment of chronic total occlusions and highly stenotic lesions within the peripheral vasculature from a radial access point.

SUMMARY OF INVENTION

The present invention provides a device for the treatment of chronic total occlusions and highly stenotic lesions within the peripheral vasculature from a radial access point, and may include, for example, an outer sheath and a hypotube ultrasonic transmission member.

The present invention in one form provides an ultrasonic catheter system having an ultrasonic transducer and a catheter assembly. The ultrasonic transducer produces vibrational energy. The catheter assembly includes an outer sheath, which has a sheath lumen, and a hypotube ultrasonic transmission member disposed in the sheath lumen. The outer sheath has a first end, a second end, and a frustoconical side wall portion located proximal to the second end. The sheath lumen extends from the first end to the second end. The hypotube ultrasonic transmission member has a hypotube side wall, a proximal hypotube portion, a distal hypotube portion, and a tapered intermediate portion. The proximal hypotube portion is operatively coupled to the ultrasonic transducer. The proximal hypotube portion has a first diameter, and the distal hypotube portion has a second diameter less than the first diameter. The tapered intermediate portion is configured to transition from the first diameter of the proximal hypotube portion to the second diameter of the distal hypotube portion. The tapered intermediate region is located proximate the frustoconical side wall portion of the outer sheath. An advantage of the present invention is that the distal hypotube portion is configured for longitudinal, transverse, or longitudinal and transverse displacement in accordance with the vibrational energy produced by the ultrasonic transducer.

The invention in one form is directed to an ultrasonic catheter system that includes an ultrasonic transducer, and outer sheath, and a hypotube ultrasonic transmission member. The outer sheath includes a first end, a second end, and a frustoconical side wall portion located proximal to the second end, and having a sheath lumen that extends from the first end to the second end. The hypotube ultrasonic transmission member is disposed in the sheath lumen of the outer sheath. The hypotube ultrasonic transmission member has a hypotube side wall, a proximal hypotube portion, a distal hypotube portion, and a tapered intermediate portion. The proximal hypotube portion is operatively coupled to the ultrasonic transducer. The proximal hypotube portion has a first diameter, and the distal hypotube portion has a second diameter less than the first diameter. The tapered intermediate portion is configured to transition from the first diameter of the proximal hypotube portion to the second diameter of the distal hypotube portion. Advantageously, the tapered intermediate region is located proximate the frustoconical side wall portion of the outer sheath.

The invention in another form is directed to a catheter assembly having an outer sheath and a hypotube ultrasonic transmission member. The outer sheath includes a first end, a second end, and a frustoconical side wall portion located proximal to the second end, and having a sheath lumen that extends from the first end to the second end. The hypotube ultrasonic transmission member is disposed in the sheath lumen of the outer sheath. The hypotube ultrasonic transmission member has a hypotube side wall, a proximal hypotube portion, a distal hypotube portion, and a tapered intermediate portion. The proximal hypotube portion is configured to be operatively coupled to an ultrasonic transducer. The proximal hypotube portion has a first diameter, and the distal hypotube portion has a second diameter less than the first diameter. The tapered intermediate portion is configured to transition from the first diameter of the proximal hypotube portion to the second diameter of the distal hypotube portion. The tapered intermediate region is located proximate the frustoconical side wall portion of the outer sheath.

An advantage of the present invention is that the catheter assembly may be utilized through various access points, including, for example, femoral contralateral, femoral ipsilateral, radial, or brachial, for treatment in the lower limb vascular.

Another advantage is that the catheter assembly is compatible with a guide wire via over the wire (OTW) or rapid exchange (RX) approaches.

Yet another advantage is that the ultrasonic catheter system may include a vacuum source for creating aspiration during ultrasonic energy activation of the hypotube ultrasonic transmission member to reduce the risk of distal embolization.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1A:
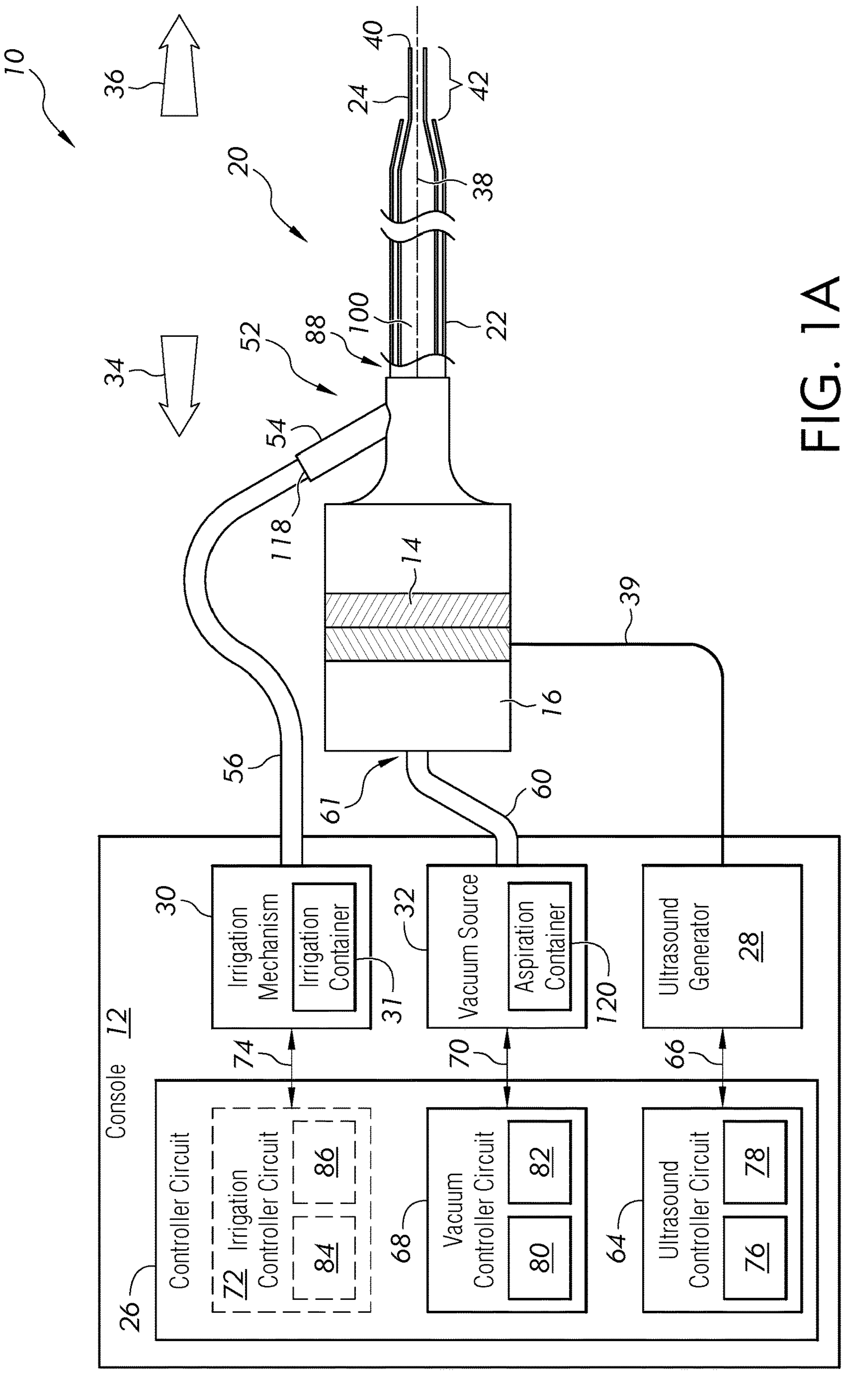
FIG. 1A is a block diagram depicting an ultrasonic catheter system that includes a console, an ultrasonic transducer, and a catheter assembly with a longitudinal portion broken away to expose an interior portion of an outer sheath and a hypotube ultrasonic transmission member of the catheter assembly.

Referring now to the drawings, and more particularly to FIG. 1A, there is shown an ultrasonic catheter system 10, which generally includes a console 12, an ultrasonic transducer 14 having a transducer lumen, a proximal end connector assembly 16 coupled with a catheter assembly 20 having an outer sheath 22 and a hypotube ultrasonic transmission member 24, which is a small profile, long metallic tube for medical application. The console 12 provides a controller circuit 26 for monitoring and controlling ultrasonic catheter system 10 and various sub-systems and functions thereof. Console 12 includes an ultrasonic generator 28 that is operatively coupled with the ultrasonic transducer 14 to provide electrical energy to ultrasonic transducer 14, which, in turn, generates and supplies ultrasonic vibrational energy to catheter assembly 20. Console 12 also includes an irrigation mechanism 30 configured to supply irrigation fluid 62 to catheter assembly 20 from an irrigation container 31. Console 12 also includes a vacuum source 32 to aspirate catheter assembly 20 by applying a vacuum 33, i.e., a negative pressure.

To assist in the description of these components of the systems, methods, and devices disclosed herein, the following coordinate terms are used. FIG. 1A shows a proximal direction 34 and a distal direction 36. The terms "proximal" and "distal", which are used to describe the present ultrasonic catheter system 10 and catheter assembly 20, are used consistently with proximal direction 34 and distal direction 36, respectively, and in each embodiment described herein. Also, as shown in FIGS. 1A, 2, 3, 4, 5, and 6, a central longitudinal axis 38 runs centrally through catheter assembly 20, 128, 150, 180, 220, 240, respectively.

Ultrasonic generator 28 is configured to convert an alternating electric current (e.g., a current associated with mains electricity) into a high-frequency current (e.g., a current with a frequency commensurate with the operating frequency of the ultrasonic transducer 14), and ultrasonic transducer 14, in turn, is configured to convert the high-frequency current into the vibrational energy. The high-frequency current passes from the ultrasonic generator 28 to the ultrasonic transducer 14 over cable 39. Generally, hypotube ultrasonic transmission member 24 transmits ultrasonic vibrational energy as a sinusoidal wave from ultrasonic transducer 14 to a hypotube distal end 40 of hypotube ultrasonic transmission member 24 to cause a distal hypotube portion 42 to vibrate.

In some embodiments, ultrasonic transducer 14 is of a Langevin type. The range of ultrasound frequency of ultrasound energy transmitted to hypotube ultrasonic transmission member 24 is 19 kilohertz (kHz) to 160 kHz. The following two modes are preferred: a first mode of 28 kHz; and a second mode of 40 kHz. When activated by the ultrasound energy, the distal hypotube portion 42 may vibrate transversely, longitudinally, or both transversely and longitudinally. Distal hypotube portion 42 is configured for longitudinal, transverse, or longitudinal and transverse displacement in accordance with the vibrational energy. This mechanical vibration of distal hypotube portion 42 may result in micromotion that results in cavitation bubbles 44, which ablate an occlusion 46, e.g., plaque, from a blood vessel 48, shown in FIGS. 1C and 1D, and performs atherectomy functions. Distal hypotube portion 42 is configured to convert the vibrational energy received from ultrasonic transducer 14 to physically have contact with the occlusion 46 to break up occlusion 46 mechanically into particles 50. Mechanically vibrating the distal hypotube portion 42 may also remove plaque by direct mechanical impact performing atherectomy and chronic total occlusion recanalization functions.

In some embodiments, console 12 can further include a foot switch (not shown) configured to activate and deactivate ultrasonic catheter system 10 such as activate and deactivate the transmission of high-frequency current from ultrasonic generator 28 to the ultrasonic transducer 14 and ultimately to hypotube ultrasonic transmission member 24 of catheter assembly 20. For example, when ultrasonic catheter system 10 is powered on but not activated, the foot switch can be used to activate ultrasonic catheter system 10, thereby activating hypotube ultrasonic transmission member 24 of catheter assembly 20. When ultrasonic catheter system 10 is powered on and activated, the foot switch can be used to deactivate the system, thereby deactivating hypotube ultrasonic transmission member 24.

Catheter assembly 20 may include proximal end connector assembly 16. Proximal end connector assembly 16 may have a Y-connector 52 with one or more side-arms 54, for example, for providing an irrigation fluid 62 via an irrigation tube 56, or for passage of a guide wire 58, or for providing vacuum 33 via a vacuum line 60 to vacuum source 32. Proximal end connector assembly 16 also includes a connector assembly proximal port 61 to which a vacuum line 60 or an irrigation tube 56 is connected, depending on the embodiment.

According to some aspects of the system, guidewire 58 may avoid the Y-connector 52 and side-arm 54 and instead extend in the proximal direction 34 and distal direction 36 through the transducer lumen of the transducer. Accordingly, from the proximal end of guide wire 58, guide wire 58 extends in distal direction 36 through the connector assembly proximal port 61 and through the transducer lumen, which cannot be seen from the perspective of FIG. 1A. Guide wire 58 extends in distal direction 36 from the transducer lumen into a hypotube lumen 100 and exits hypotube lumen 100 at hypotube distal end 40 of hypotube ultrasonic transmission member 24. Guide wire 58 has a proximal end that is proximal of the connector assembly proximal port 61 and a distal end that is distal of the hypotube distal end 40.

Figure 1B:
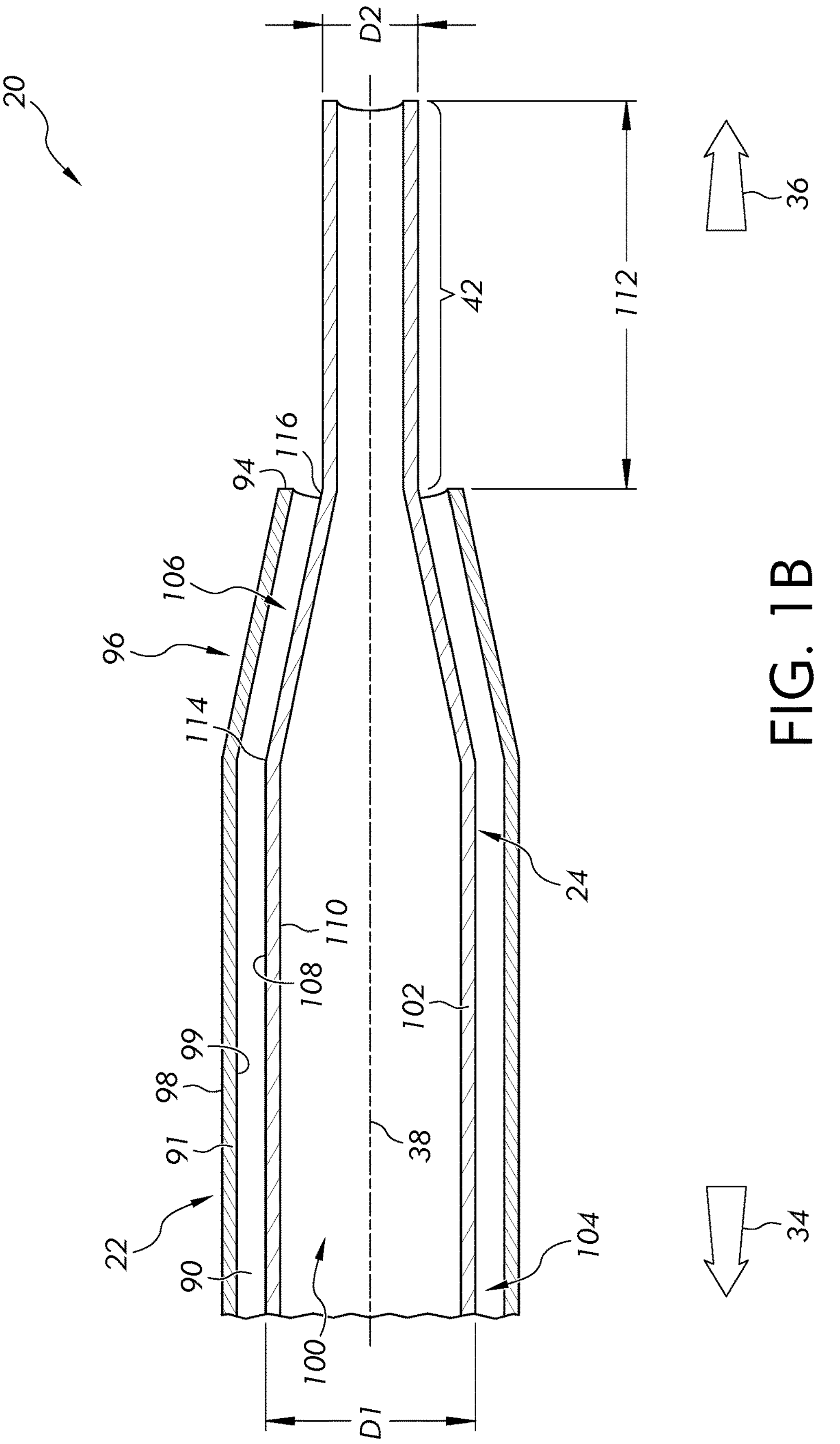
FIG. 1B is a longitudinal cross-sectional side view of a portion of the catheter assembly of the ultrasonic catheter system of FIG. 1A, according to an embodiment of the present invention.
Figure 1C:
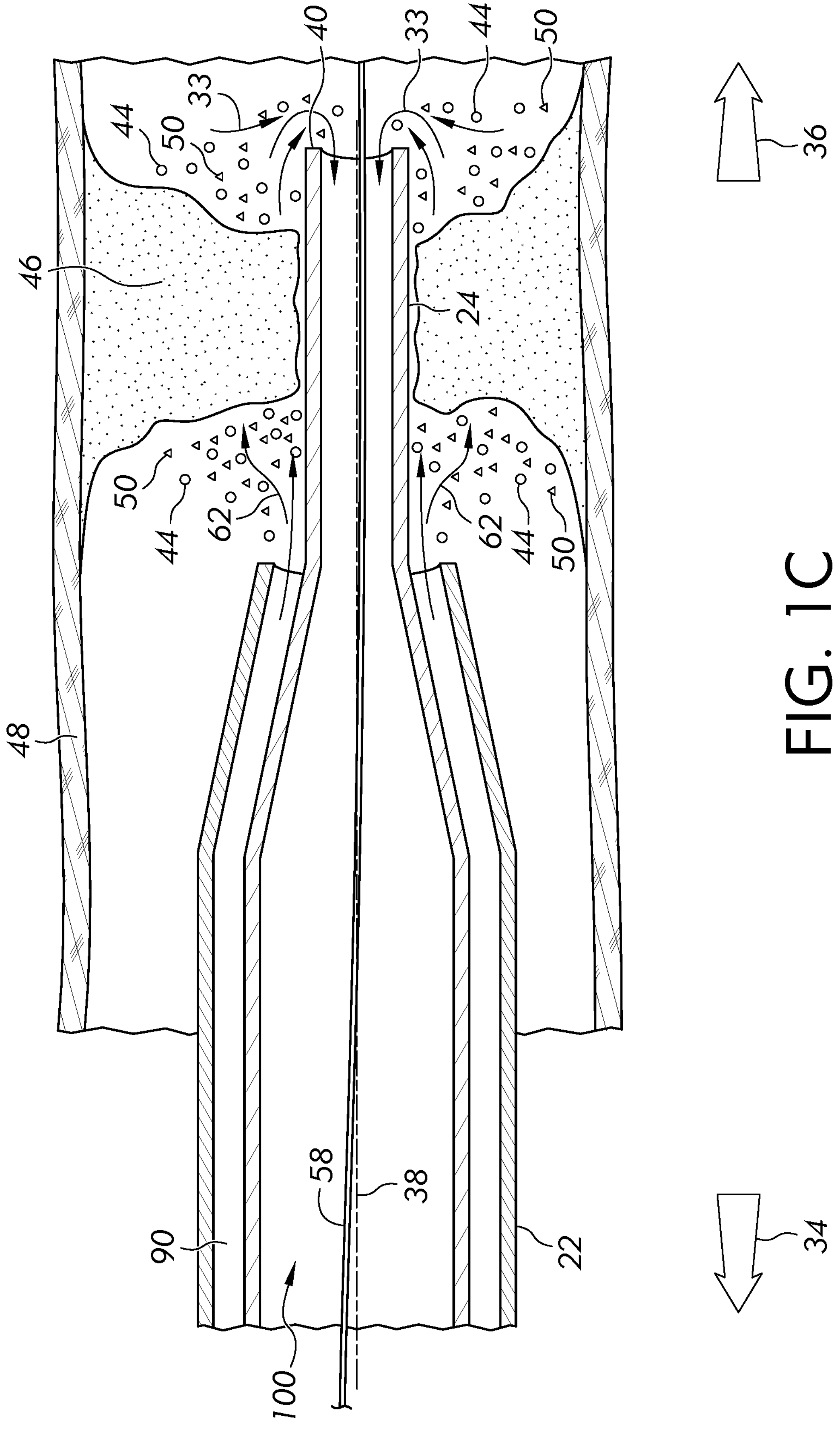
FIG. 1C is a cutaway, partially cross-sectional side view of a portion of the catheter assembly of FIG. 1B positioned in an occluded blood vessel, illustrating the operation of the catheter assembly according to one aspect of the ultrasonic catheter system.
Figure 1D:
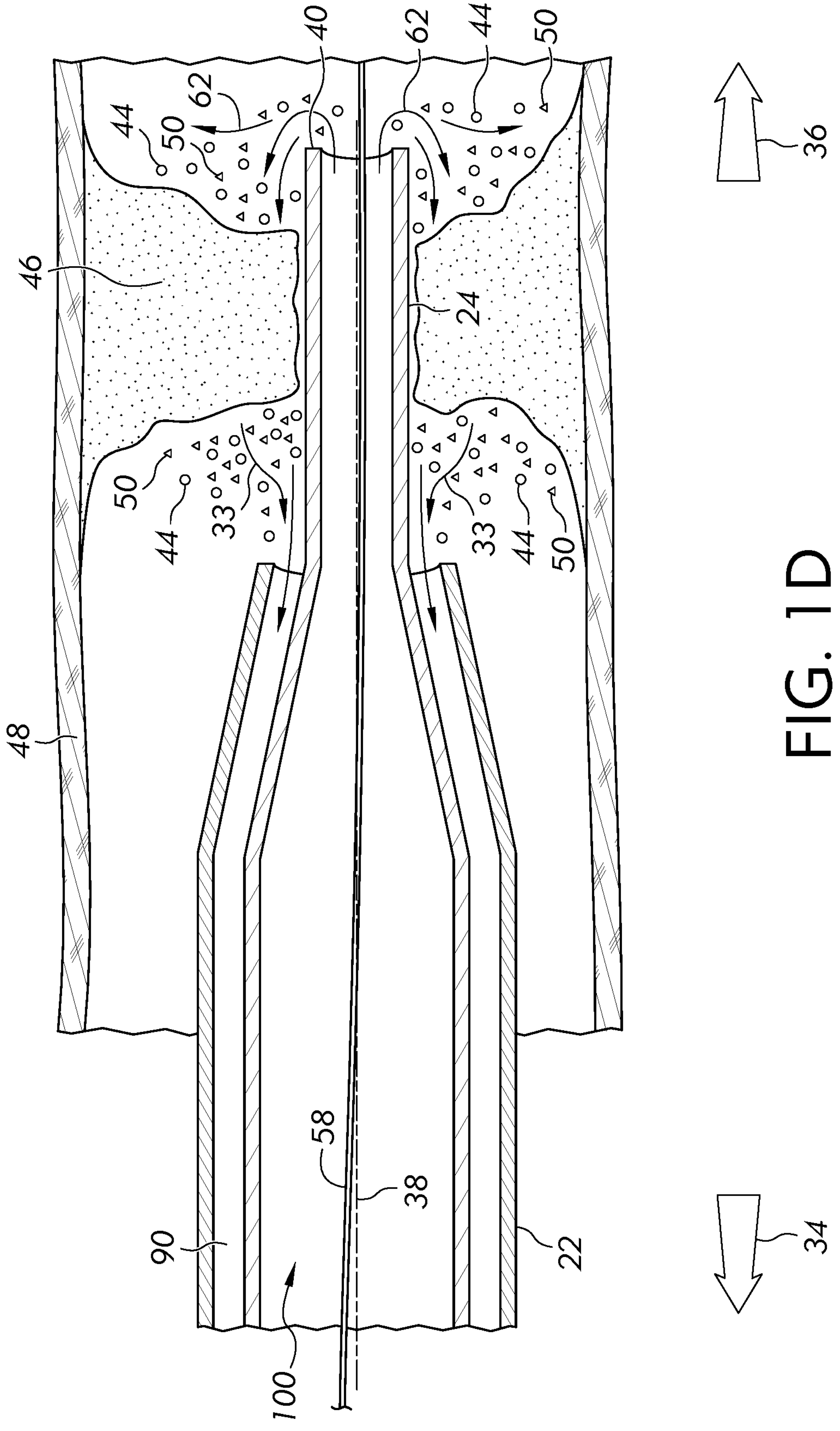
FIG. 1D is a cutaway, partially cross-sectional side view of a portion of the catheter assembly of FIG. 1B positioned in the occluded blood vessel, illustrating the operation of the catheter assembly according to another aspect of the ultrasonic catheter system.

Whether vacuum 33 is applied through vacuum line 60 being directly connected to the transducer lumen via connector assembly proximal port 61 or vacuum 33 is applied through vacuum line 60 being directly connected to side-arm 54, because vacuum 33 is a negative pressure, when vacuum 33 is applied in distal direction 36, vacuum 33, as shown in FIGS. 1C and 1D, pulls in proximal direction 34 toward vacuum source 32 and aspiration container 120, as shown in FIG. 1A.

In some embodiments, irrigation mechanism 30 is a roller pump, and in others, irrigation mechanism 30 is an injector. In either embodiment, irrigation mechanism 30 is configured to supply an irrigation fluid 62 into hypotube ultrasonic transmission member 24 of catheter assembly 20. Whether irrigation tube 56 is connected to the transducer lumen, as in the embodiment of FIG. 1D, or irrigation tube 56 is connected to side-arm 54, as in the embodiments of FIGS. 1A and 1C, irrigation fluid 62, e.g. sterile saline, is delivered in a distal direction for irrigating an anatomical area undergoing an intravascular lesion-modification procedure (e.g., ultrasound-based atherectomy), cooling hypotube ultrasonic transmission member 24 of catheter assembly 20, lubricating catheter assembly 20 to reduce friction between hypotube ultrasonic transmission member 24 and guide wire 58, or a combination thereof. Any suitable biocompatible fluid may be used as irrigation fluid 62 to be passed through irrigation tube 56 and catheter assembly 20, such as refrigerated fluid, lubricious fluid, drug-containing fluid, supersaturated saline or contrast/saline mixture, or the like. In some embodiments, console 12 can further include a switch (not shown) configured to activate and deactivate irrigation mechanism 30 to control the flow of irrigation fluid 62 to catheter assembly 20.

It should be emphasized that catheter assembly 20 of the present invention may be used with any suitable proximal devices, such as any suitable ultrasonic transducer 14 or ultrasonic generator 28. Therefore, exemplary FIG. 1A and any following descriptions of proximal apparatus or systems for use with catheter assemblies should in no way be interpreted to limit the scope of the present invention as defined in the appended claims.

As shown in FIG. 1A, controller circuit 26 includes an ultrasound controller circuit 64 that is communicatively coupled to ultrasonic generator 28 via a first communication link 66, which may be wired or wireless. Controller circuit 26 further includes a vacuum controller circuit 68 that is communicatively coupled to the vacuum source 32 via a second communication link 70, which may be wired or wireless. Optionally, controller circuit 26 includes an irrigation controller circuit 72 that is communicatively coupled to irrigation mechanism 30 via a third communication link 74, which may be wired or wireless. Alternatively, irrigation mechanism 30 is entirely manually and mechanically controlled and controller circuit 26, in this alternative embodiment, would not include the irrigation controller circuit 72.

Console 12 and controller circuit 26 may include a user interface, e.g., in the form of operator buttons and/or a touch screen display. Ultrasound controller circuit 64 may be assembled on an electrical circuit board and includes a first processor circuit 76 and a first memory circuit 78. Ultrasound controller circuit 64 may be a commercially available microcontroller, or alternatively, may be formed as one or more Application Specific Integrated Circuits (ASIC). First processor circuit 76 includes one or more programmable microprocessors and associated circuitry, such as an input/output interface, clock, buffers, non-transitory electronic memory, etc. First memory circuit 78 is communicatively coupled to first processor circuit 76, e.g., via a bus circuit, and is a non-transitory electronic memory that may include volatile memory circuits, such as random access memory (RAM), and non-volatile memory circuits, such as read only memory (ROM), electronically erasable programmable ROM (EEPROM), NOR flash memory, NAND flash memory, etc.

Ultrasound controller circuit 64 is configured via software and/or firmware to execute program instructions to perform functions, such as effecting ultrasound vibrational energy to be transmitted ultimately to hypotube distal end 40 of hypotube ultrasonic transmission member 24 of catheter assembly 20 (see also FIGS. 1B-1D).

Vacuum controller circuit 68 is assembled on an electrical circuit board and includes a second processor circuit 80 and a second memory circuit 82. Vacuum controller circuit 68 may be a commercially available microcontroller, or alternatively, may be formed as one or more Application Specific Integrated Circuits (ASIC). Second processor circuit 80 includes one or more programmable microprocessors and associated circuitry, such as an input/output interface, clock, buffers, non-transitory electronic memory, etc. Second memory circuit 82 is communicatively coupled to second processor circuit 80, e.g., via a bus circuit, and is a non-transitory electronic memory that may include volatile memory circuits, such as random access memory (RAM), and non-volatile memory circuits, such as read only memory (ROM), electronically erasable programmable ROM (EEPROM), NOR flash memory, NAND flash memory, etc.

Vacuum controller circuit 68 is configured via software and/or firmware to execute program instructions to perform functions, such as effecting vacuum source 32 to aspirate catheter assembly 20 and blood vessel 48 of particles 50 (see FIGS. 1C and 1D) via applying vacuum 33 to vacuum line 60.

According to one aspect of controller circuit 26, controller circuit 26 includes irrigation controller circuit 72. Irrigation controller circuit 72 may be assembled on an electrical circuit board and includes a third processor circuit 84 and a third memory circuit 86. Irrigation controller circuit 72 may be a commercially available microcontroller, or alternatively, may be formed as one or more Application Specific Integrated Circuits (ASIC). Third processor circuit 84 includes one or more programmable microprocessors and associated circuitry, such as an input/output interface, clock, buffers, non-transitory electronic memory, etc. Third memory circuit 86 is communicatively coupled to the third processor circuit 84, e.g., via a bus circuit, and is a non-transitory electronic memory that may include volatile memory circuits, such as random access memory (RAM), and non-volatile memory circuits, such as read only memory (ROM), electronically erasable programmable ROM (EEPROM), NOR flash memory, NAND flash memory, etc.

Irrigation controller circuit 72 is configured via software and/or firmware to execute program instructions to perform functions, such as effecting control of the supply of irrigation fluid 62 to catheter assembly 20 via irrigation tube 56.

FIG. 1B shows a cross-sectional side view of a portion of catheter assembly 20 in accordance with some embodiments. Hypotube ultrasonic transmission member 24 and outer sheath 22 extend along central longitudinal axis 38. A hypotube proximal end 88 of the proximal portion of hypotube ultrasonic transmission member 24 may be coupled to ultrasonic transducer 14 by a sonic connector (not shown) or by an intervening ultrasonic horn (not shown). Stated differently, hypotube ultrasonic transmission member 24 may be coupled to ultrasonic generator 28 via ultrasonic transducer 14 and any intervening connectors.

Outer sheath 22 has a sheath lumen 90 formed by a sheath side wall 91. Outer sheath 22 includes an outer sheath first end 92, an outer sheath second end 94, and a frustoconical side wall portion 96 located proximal to the outer sheath second end 94 and distal of the outer sheath first end 92. Sheath lumen 90 extends from outer sheath first end 92 (as shown in FIG. 1A) to outer sheath second end 94. Outer sheath first end 92 is proximal to outer sheath second end 94. Furthermore, sheath side wall 91 has a sheath exterior surface 98 and a sheath interior surface 99. Outer sheath 22 is made from a flexible material. Some examples of suitable flexible materials include PEBAX®, GRILAMID®, polyimide, nylon, silicone, or other materials known in the art.

Hypotube ultrasonic transmission member 24 is disposed in sheath lumen 90 of outer sheath 22. Yet, distal hypotube portion 42 is the active portion of hypotube ultrasonic transmission member 24 that extends distally beyond outer sheath second end 94 of outer sheath 22. Hypotube ultrasonic transmission member 24 has a hypotube lumen 100, a hypotube side wall 102, a proximal hypotube portion 104, distal hypotube portion 42, and a tapered intermediate portion 106. Hypotube side wall 102 includes a hypotube exterior surface 108 and a hypotube interior surface 110. Hypotube lumen 100 runs the entire length of hypotube ultrasonic transmission member 24 from hypotube proximal end 88 (shown in FIG. 1A) to hypotube distal end 40. Proximal hypotube portion 104 is operatively coupled to the ultrasonic transducer 14 at hypotube proximal end 88. Proximal hypotube portion 104 has a first diameter D1. Distal hypotube portion 42 has a second diameter D2 that is less than the first diameter D1 of the proximal hypotube portion 104.

Catheter assembly 20 of FIG. 1B is not drawn to scale and may have any number of suitable proportions and scale. Tapered intermediate portion 106 and distal hypotube portion 42 may have different proportions relative to each other than what is shown in FIG. 1B. Distal hypotube portion 42 has a distal hypotube portion length 112 in the range of 5 millimeters to 20 centimeters.

Figure 3:
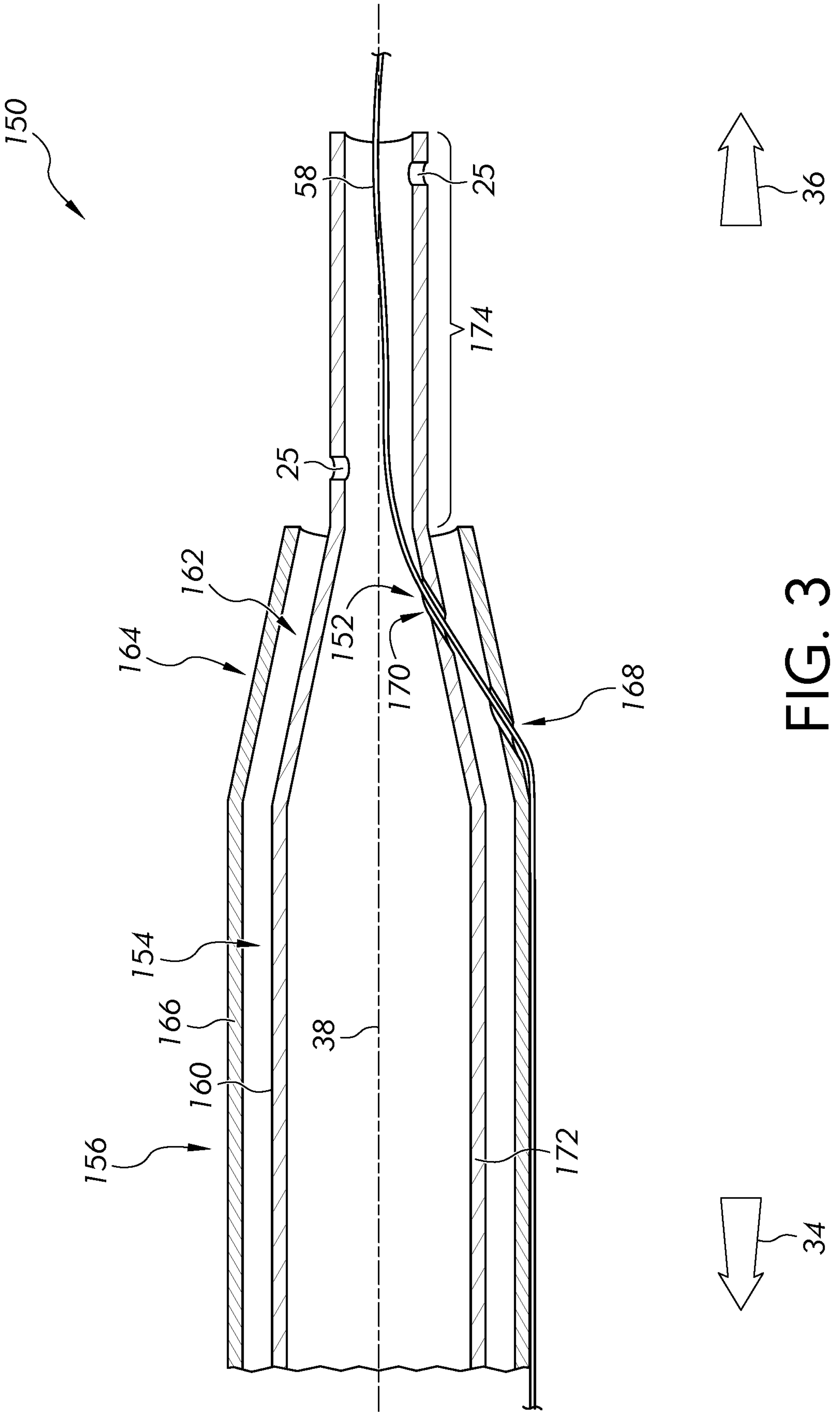
FIG. 3 is a longitudinal cross-sectional side view of a portion of a catheter assembly according to another embodiment of the present invention.

Hypotube ultrasonic transmission member 24 is made from suitable flexible metals, such as, nitinol and titanium. In addition, there are advantages to making hypotube ultrasonic transmission member 24, and, in particular, distal hypotube portion 42 from a magnetic material. According to some aspects, distal hypotube portion 42 includes one or more abrasive elements. Alternatively, distal hypotube portion 42 includes an abrasive distal hypotube exterior surface. Additionally or alternatively, hypotube ultrasonic transmission member 24 includes a plurality of holes, as best seen in FIG. 3, through the hypotube side wall 102 in distal hypotube portion 42. The plurality of holes 25 located in distal hypotube portion 42 are configured for creating cavitation bubbles 44 to ablate vascular occlusions 46. Alternatively, according to some aspects, hypotube ultrasonic transmission member 24 does not include any holes through hypotube side wall 102 in distal hypotube portion 42.

Tapered intermediate portion 106 has a tapered intermediate portion proximal end 114 and a tapered intermediate portion distal end 116. Tapered intermediate portion 106 transitions from first diameter D1 of the proximal hypotube portion 104 to second diameter D2 of distal hypotube portion 42. Tapered intermediate portion 106 is located proximate the frustoconical side wall portion 96 of outer sheath 22. The length of the tapered intermediate portion 106 varies. Tapered intermediate portion 106 tapers from first diameter D1 of the proximal hypotube portion 104 to second diameter D2 of distal hypotube portion 42, in which first diameter D1 is greater than second diameter D2. In other words, tapered intermediate portion 106 has a taper that narrows from proximal hypotube portion 104 to distal hypotube portion 42. Tapered intermediate portion 106 has a frustoconical shape as it extends and narrows in distal direction 36 from proximal hypotube portion 104 to distal hypotube portion 42.

In one aspect of the present design, first diameter D1 of proximal hypotube portion 104 is constant. In this aspect, the measurement of any diameter measured at any point along proximal hypotube portion 104 will be equal to the measurement of any other diameter measured at any point along proximal hypotube portion 104. Proximal hypotube portion 104 has the form of a hollow cylinder.

Generally, second diameter D2 of distal hypotube portion 42 is constant across distal hypotube portion 42. Accordingly, the measurement of any diameter taken at any point along the distal hypotube portion 42 will be equal to the measurement of any other diameter taken at any point along distal hypotube portion 42. Distal hypotube portion 42 has the form of a hollow cylinder.

Tapered intermediate portion 106 connects proximal hypotube portion 104 to distal hypotube portion 42. Hypotube ultrasonic transmission member 24 may be constructed of the same material from hypotube proximal end 88 of hypotube ultrasonic transmission member 24 to hypotube distal end 40 of hypotube ultrasonic transmission member 24. Proximal hypotube portion 104 of hypotube ultrasonic transmission member 24 extends in proximal direction 34 from tapered intermediate portion proximal end 114 of tapered intermediate portion 106. Proximal hypotube portion 104 extends evenly in a proximal direction 34 along the central longitudinal axis 38 from tapered intermediate portion proximal end 114. Distal hypotube portion 42 of hypotube ultrasonic transmission member 24 extends in distal direction 36 from tapered intermediate portion distal end 116 of the tapered intermediate portion 106. Distal hypotube portion 42 extends evenly in distal direction 36 along the central longitudinal axis 38 from tapered intermediate portion distal end 116.

Under one aspect of ultrasonic catheter system 10, irrigation tube 56 has an irrigation tube distal end 118 that is connected directly to a port, such as side arm 54, of proximal end connector assembly 16. In this embodiment and as shown in FIG. 1C, the irrigation fluid 62 is directed to sheath lumen 90 between sheath interior surface 99 of outer sheath 22 and hypotube exterior surface 108 of hypotube ultrasonic transmission member 24. Additionally, according to this aspect of the system, ultrasonic transducer 14 includes a transducer lumen, which cannot be shown in a cross-sectional view taken lengthwise along the central longitudinal axis 38. Vacuum source 32 is coupled to the transducer lumen via vacuum line 60. Hypotube ultrasonic transmission member 24 aspirates all fluid and particles 50 through hypotube lumen 100 of hypotube ultrasonic transmission member 24 to an aspiration container 120 via vacuum 33, as shown in FIG. 1C. Particles 50 are any remaining pieces of the ablated occlusion 46 or lesion, i.e., free-floating calcification particles. Moreover, in the embodiments in which catheter assembly 20 includes a plurality of holes 25 located in distal hypotube portion 42, the plurality of holes are configured for aspirating particles 50 through the hypotube lumen 100 in proximal direction 34 by vacuum 33 applied to catheter assembly 20 at the proximal end of ultrasonic transducer 14. As the distal hypotube portion 42 experiences mechanical vibration, the resulting micromotion creates cavitation bubbles 44. The friction from the mechanical vibration of distal hypotube portion 42 against occlusion 46 and the friction from cavitation bubbles 44 cause occlusion 46 to be ablated from blood vessel 48 and to create space between occlusion 46 and hypotube exterior surface 108. As occlusion 46 breaks down, the plurality of particles 50 shown in FIG. 1C as being proximal of occlusion 46, are able to pass by occlusion 46, around hypotube distal end 40, and through hypotube lumen 100 of hypotube ultrasonic transmission member 24 in proximal direction 34 to an aspiration container 120 via vacuum 33. Aspiration of particles 50 reduces the risk of distal remobilization.

Alternatively, according to an aspect of the system using the catheter assembly of FIG. 1D, irrigation tube distal end 118 of irrigation tube 56 is connected to the proximal end of ultrasonic transducer 14 having the transducer lumen. In this embodiment, irrigation fluid 62 supplied from irrigation mechanism 30 and irrigation container 31 passes through irrigation tube 56, then through the transducer lumen, and then through hypotube lumen 100 of hypotube ultrasonic transmission member 24. Additionally, according to this aspect of the system, vacuum line 60 is coupled to a port, such as side arm 54, in proximal end connector assembly 16 to aspirate the sheath lumen 90 between outer sheath 22 and hypotube ultrasonic transmission member 24 by applying vacuum 33. In particular, in this aspect of the system, vacuum controller circuit 68 controls vacuum source 32 to aspirate fluid and particles 50 in the space that exists between sheath interior surface 99 and hypotube exterior surface 108. As distal hypotube portion 42 mechanically vibrates and produces cavitation bubbles 44, occlusion 46 breaks down further and breaks away from hypotube exterior surface 108. As such, occlusion 46 becomes smaller, there is a fluid path that permits particles 50, including particles 50 shown to be distal of occlusion 46 in FIG. 1D, to pass through sheath lumen 90 between sheath interior surface 99 and hypotube exterior surface 108 in proximal direction 34.

Figure 2:
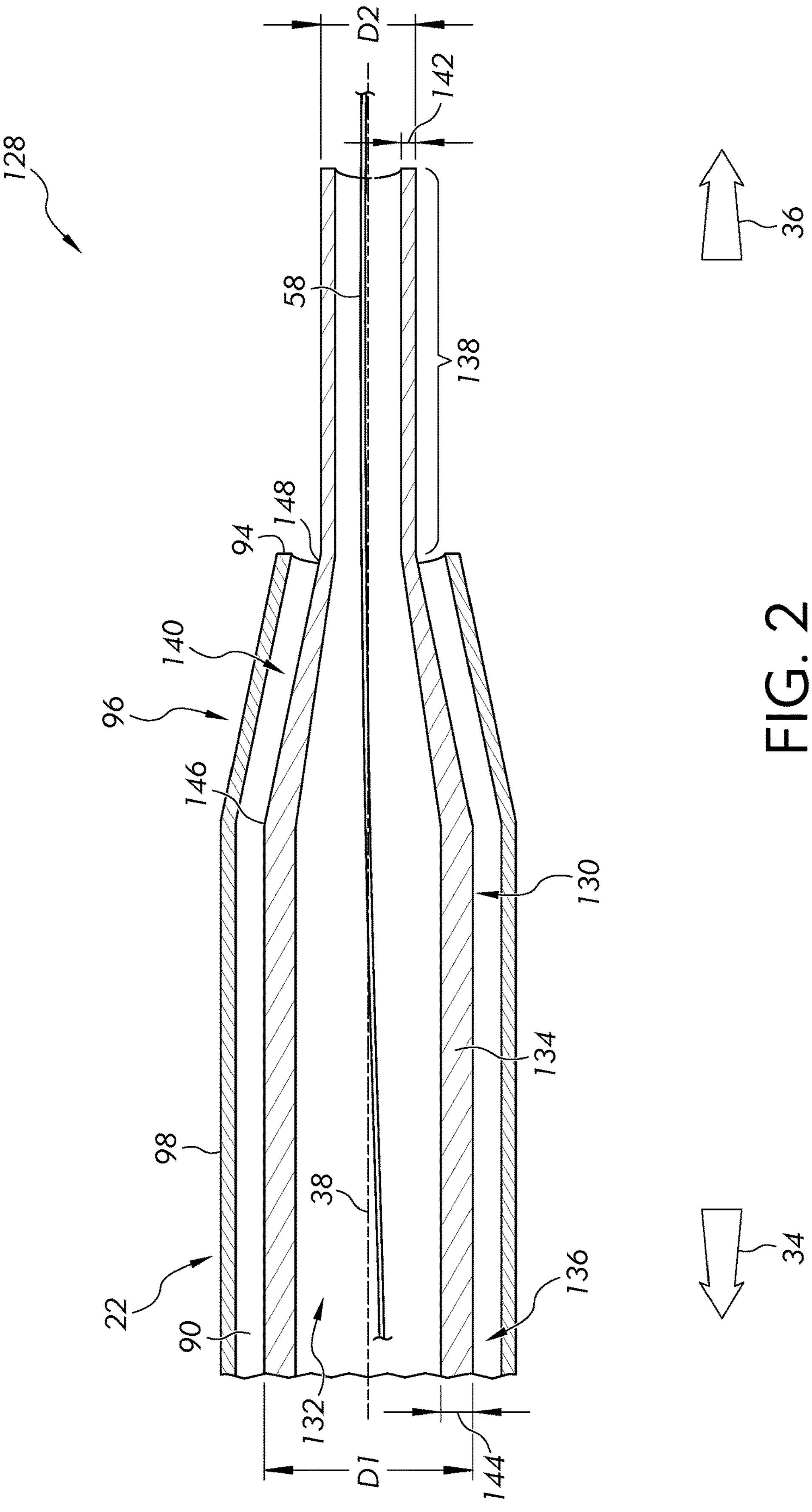
FIG. 2 is a longitudinal cross-sectional side view of a portion of a catheter assembly according to another embodiment of the present invention.

FIG. 2 shows another embodiment of catheter assembly 20 in accordance with an aspect of the present invention, wherein hypotube ultrasonic transmission member 24 of FIG. 1B is replaced with a hypotube ultrasonic transmission member 130, to thereby define a catheter assembly 128, which includes hypotube ultrasonic transmission member 130 and outer sheath 22. Like catheter assembly 20 in FIG. 1A, catheter assembly 128 is configured for use with console 12 and proximal end connector assembly 16.

Hypotube ultrasonic transmission member 130 is disposed in sheath lumen 90 of outer sheath 22. Hypotube ultrasonic transmission member 130 has a hypotube lumen 132, a hypotube side wall 134, a proximal hypotube portion 136, a distal hypotube portion 138, and a tapered intermediate portion 140. Hypotube ultrasonic transmission member 130 includes distal hypotube portion 138 that extends distally beyond outer sheath second end 94 of outer sheath 22.

Furthermore, as in the description of hypotube ultrasonic transmission member 24 of FIGS. 1A-ID, a first diameter, shown in FIG. 2 as D1, measured at any point along proximal hypotube portion 136 of hypotube ultrasonic transmission member 130 is larger than a second diameter, shown in FIG. 2 as D2, measured at distal hypotube portion 138 since a tapered intermediate portion 140 narrows uniformly along central longitudinal axis 38 toward distal direction 36.

Referring to FIG. 2, a first thickness 142 of the hypotube side wall 134 at the distal hypotube portion 138 is less than a second thickness 144 of the hypotube side wall 134 at the proximal hypotube portion 136 of the hypotube ultrasonic transmission member 130. The measurement of the depth or thickness of the hypotube side wall 134 transitions in tapered intermediate portion 140. The thickness of the hypotube side wall 134 tapers from thicker to thinner from a tapered intermediate portion proximal end 146 to a tapered intermediate portion distal end 148. Hypotube ultrasonic transmission member 130 tapers or narrows its profile in two ways over the length of tapered intermediate portion 140 as hypotube ultrasonic transmission member 130 extends in the distal direction 36 from the proximal hypotube portion 136: (1) in thickness of the hypotube side wall 134; and (2) in diameter, as shown in FIG. 2 from D1 to D2. More particularly, a first measurement of the depth of hypotube side wall 134 taken along an axis that is transverse to central longitudinal axis 38 at a tapered intermediate portion proximal end 146 is longer than a second measurement of the depth of the hypotube side wall 134 taken along an axis that is transverse to central longitudinal axis 38 at a tapered intermediate portion distal end 148.

In some embodiments, such as, those of FIGS. 1B and 2, ultrasonic catheter system 10 includes a guide wire, such as, guide wire 58. For the sake of brevity, FIG. 2 will be described with guide wire 58, but the following also applies to the embodiment of FIG. 1B. Guide wire 58 is centrally located within hypotube lumen 132 in FIG. 2. The outer diameter of guide wire 58 is in the range of 0.009 inches to 0.035 inches. Generally, ultrasonic catheter system 10 and catheter assembly 128 do not include a guide wire tube or a separate guide wire lumen, and ultrasonic transducer 14 has a transducer lumen (not shown) that extends along central longitudinal axis 38. The transducer lumen of ultrasonic transducer 14 provides a passage for guide wire 58 and irrigation fluid 62 to enter the hypotube ultrasonic transmission member 130 through ultrasonic transducer 14. In these embodiments, the roller pump or injector of the irrigation mechanism 30 is configured to provide irrigation fluid 62, e.g., saline, to catheter assembly 128 through the transducer lumen (not shown). Advantageously, the entirety of the catheter assembly 128 can be narrower for smaller vascular regions. The diameter of the hypotube ultrasonic transmission member 130 may be between one (1) millimeter and six (6) millimeters. The catheter assembly 128 is simpler to use, uses less material, and is cheaper to manufacture.

Furthermore, hypotube ultrasonic transmission member 130 becomes more flexible and easier to steer with the progressive, gradual tapering of hypotube ultrasonic transmission member 130 over the length of tapered intermediate portion 140.

FIG. 3 is another embodiment of the catheter assembly 20 in accordance with an aspect of the present invention, wherein the catheter assembly 20 of FIGS. 1A and 1B is replaced with a catheter assembly 150 of FIG. 3. Like catheter assembly 20 in FIG. 1A, catheter assembly 150 is configured for use with console 12 and proximal end connector assembly 16.

In the embodiment of FIG. 3, ultrasonic transducer 14 may be solid or may include the transducer lumen described above with regard to FIGS. 1B and 2. In catheter assembly 150 of FIG. 3, a rapid exchange port 152 is included as part of a hypotube ultrasonic transmission member 154 and an outer sheath 156. Rapid exchange port 152 extends through a hypotube side wall 172 of hypotube ultrasonic transmission member 154 and through a catheter outer sheath side wall 166 of outer sheath 156. A guide wire 58 is disposed longitudinally along an exterior surface 160 of hypotube ultrasonic transmission member 154 for a portion of the hypotube length. In the present embodiment for catheter assembly 150, for example, rapid exchange port 152 is formed in a hypotube side wall 172 of tapered intermediate portion 162 and in a frustoconical side wall portion 164 of outer sheath 156.

Rapid exchange port 152 includes a first port 168 and a second port 170. In the present embodiment, catheter assembly 150 includes outer sheath 156 having catheter outer sheath side wall 166 and first port 168 that extends through catheter outer sheath side wall 166. Second port 170 extends through hypotube side wall 172 of hypotube ultrasonic transmission member 154. In catheter assembly 150 of FIG. 3, first port 168 is located in frustoconical side wall portion 164 of outer sheath 156, and second port 170 is located in tapered intermediate portion 162 of hypotube ultrasonic transmission member 154. A distal hypotube portion 174 is the portion of hypotube ultrasonic transmission member 154 that is activated with vibrational energy from ultrasonic transducer 14. Distal hypotube portion 174 includes a plurality of holes 25 configured for creating cavitation bubbles 44 to ablate vascular occlusions 46.

According to other aspects of ultrasonic catheter system 10, instead of rapid exchange port 152 as in the embodiment of FIG. 3, a guide wire tube is connected directly to hypotube exterior surface 108 of hypotube ultrasonic transmission member 24.

Figure 4:
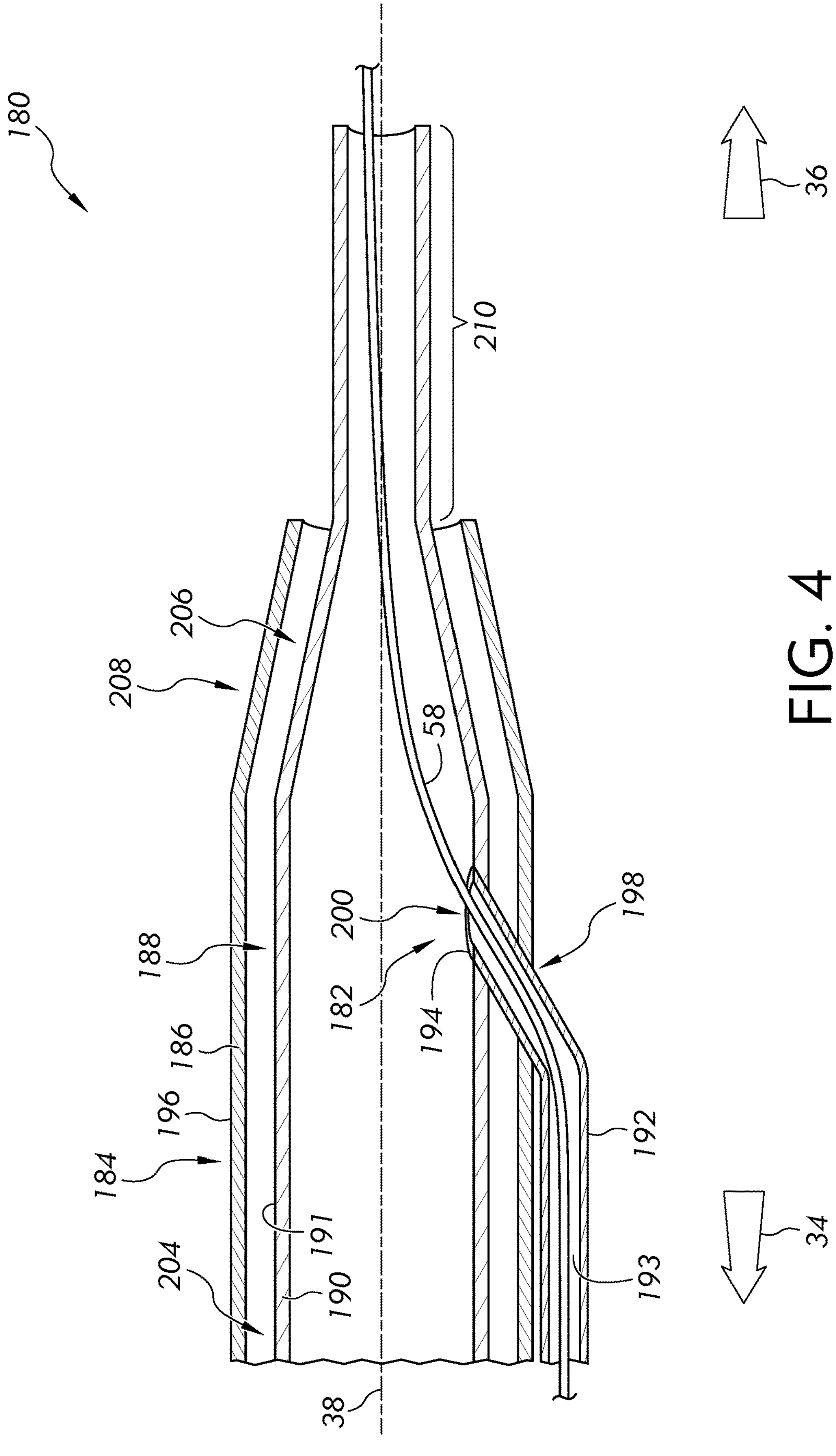
FIG. 4 is a longitudinal cross-sectional side view of a portion of a catheter assembly according to another embodiment of the present invention.

FIG. 4 is another embodiment of catheter assembly 20 in accordance with an aspect of the present invention, wherein catheter assembly 20 of FIGS. 1A and 1B is replaced with a catheter assembly 180 of FIG. 4. Like catheter assembly 20 in FIG. 1A, catheter assembly 180 is configured for use with console 12 and proximal end connector assembly 16.

In the embodiment of FIG. 4, ultrasonic transducer 14 may be solid or may include the transducer lumen described above with regard to FIGS. 1B and 2. Catheter assembly 180 includes a rapid exchange port 182. Catheter assembly 180 includes an outer sheath 184, which has a catheter outer sheath side wall 186, and a hypotube ultrasonic transmission member 188, which has a hypotube side wall 190. Catheter assembly 180 further includes an exterior guide wire tube 192, which includes a guide wire lumen 193, that extends along catheter outer sheath side wall 186 from a proximal end (not shown) of outer sheath 184 to rapid exchange port 182 at an exterior guide wire tube distal end 194. In some embodiments, not shown in FIG. 4, the exterior guide wire tube 192 is formed integrally with catheter outer sheath side wall 186 so that they share a side wall where the two meet along a outer sheath exterior surface 196 of outer sheath 184.

Rapid exchange port 182 extends through catheter outer sheath side wall 186 at an exterior port 198, and rapid exchange port 182 extends through hypotube side wall 190 at an interior port 200. Rapid exchange port 182 is configured for guide wire 58 to be extended therethrough. Guide wire 58 is configured to extend through the exterior port 198 and the interior port 200, which collectively form rapid exchange port 182. Guide wire second end is distal of a distal hypotube portion 210.

According to some aspects, rapid exchange port 182 is formed in hypotube side wall 190 of proximal hypotube portion 204, as shown in FIG. 4. Alternatively, rapid exchange port 182 is formed in a tapered intermediate portion 206 of hypotube ultrasonic transmission member 188 and a frustoconical side wall portion 208 of outer sheath 184, similar to rapid exchange port 152 shown in FIG. 3, but in the embodiment of FIG. 4 exterior guide wire tube 192 is coupled to rapid exchange port 152. Rapid exchange port 152 is connected directly to a hypotube exterior surface 191. Still in other aspects, rapid exchange port 182 is formed in the hypotube side wall 190 of distal hypotube portion 210. Guide wire 58 extends through rapid exchange port 182. Rapid exchange port 182 allows catheter assembly 180 to use guide wire 58 of a standard length, i.e. 300 cm, versus an over-the-wire style guide wire system, which would require a longer guide wire specific for such a system. When hypotube ultrasonic transmission member 188 is made from a magnetic material, it is advantageous for guide wire 58 to be made of a magnetic material.

Figure 5:
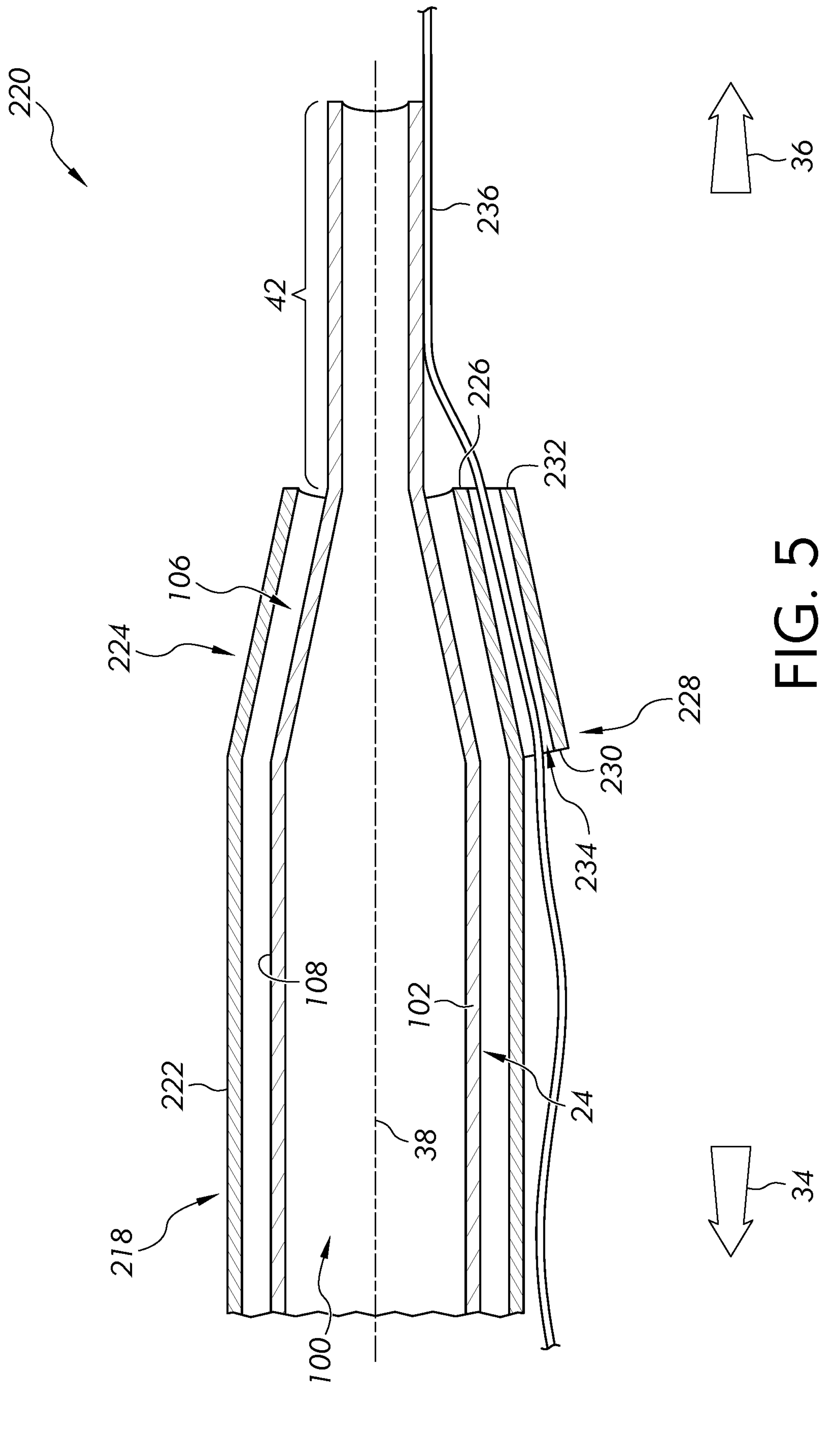
FIG. 5 is a longitudinal cross-sectional side view of a portion of a catheter assembly according to another embodiment of the present invention.

FIG. 5 is another embodiment of the catheter assembly 20 in accordance with an aspect of the present invention, wherein outer sheath 22 of catheter assembly 20 of FIGS. 1A and 1B is replaced with an outer sheath 218 to thereby define a catheter assembly 220. Like catheter assembly 20 in FIG. 1A, catheter assembly 220 is configured for use with console 12 and proximal end connector assembly 16. In the embodiment of FIG. 5, ultrasonic transducer 14 may be solid or may include the transducer lumen described above with regard to FIGS. 1B and 2.

According to catheter assembly 220 shown in FIG. 5, ultrasonic catheter system 10 includes outer sheath 218 and hypotube ultrasonic transmission member 24. Outer sheath 218 has a catheter outer sheath exterior surface 222, a frustoconical side wall portion 224, an outer sheath distal end 226, and a rapid exchange port 228. Rapid exchange port 228 of FIG. 5 has a rapid exchange port first end 230, a rapid exchange port second end 232, and a guide wire lumen 234 formed in part with catheter outer sheath exterior surface 222. Guide wire lumen 234 is connected to and integrally formed with outer sheath distal end 226 of outer sheath 218. As shown in FIG. 5, rapid exchange port 228 is formed with catheter outer sheath exterior surface 222 of frustoconical side wall portion 224.

According to other aspects, guide wire lumen 234 is connected to and integrally formed with hypotube exterior surface 108 at distal hypotube portion 42. Moreover, according to some aspects, including catheter assembly 220 shown in FIG. 5, distal hypotube portion 42 is made from magnetic material. FIG. 5 shows a magnetic guide wire 236 magnetically coupled via magnetic attraction to distal hypotube portion 42.

In any embodiment in which guide wire 58 is made of a magnetic material, such as magnetic guide wire 236, ideally, it is advantageous to provide a surface coating of Teflon or silicone to reduce the friction between guide wire 58 and catheter assembly 20 or to reduce the friction between magnetic guide wire 236 and catheter assembly 220.

In some embodiments, exterior guide wire tube 192 of FIG. 4 or rapid exchange port 228 of FIG. 5 is connected directly to hypotube exterior surface 108.

Figure 6:
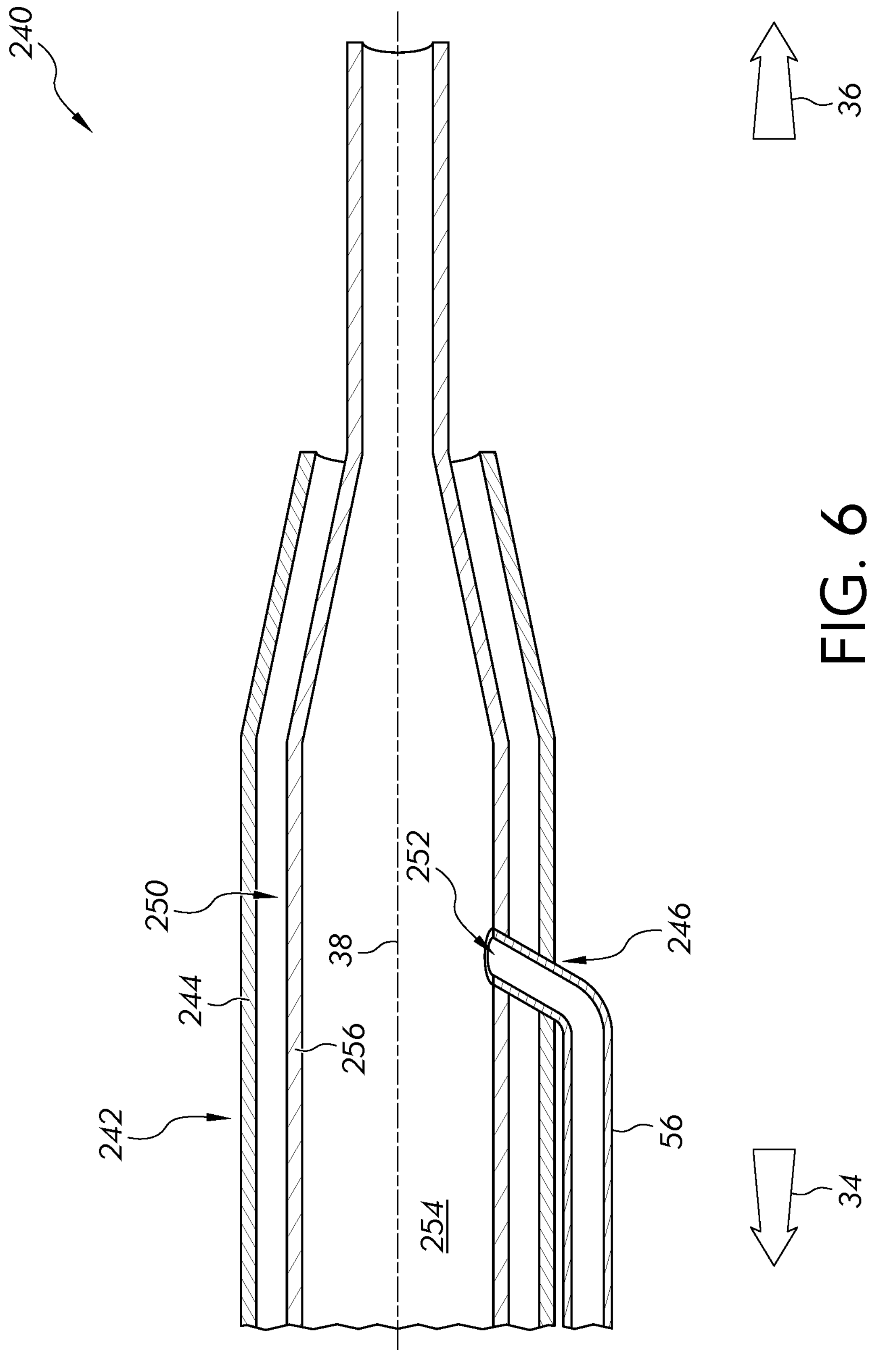
FIG. 6 is a longitudinal cross-sectional side view of a portion of a catheter assembly according to another embodiment of the present invention.

FIG. 6 is another embodiment of catheter assembly 20 in accordance with an aspect of the present invention, wherein catheter assembly 20 of FIGS. 1A and 1B is replaced with a catheter assembly 240. Like catheter assembly 20 in FIG. 1A, catheter assembly 240 is configured for use with console 12 and proximal end connector assembly 16. In the embodiment of FIG. 6, ultrasonic transducer 14 may be solid or may include the transducer lumen described above with regard to FIGS. 1B and 2.

Referring now to FIG. 6, an outer sheath 242 has a sheath side wall 244 and a first irrigation port 246 extending through sheath side wall 244. A hypotube ultrasonic transmission member 250 has a second irrigation port 252 extending through hypotube side wall 256. Irrigation tube 56 is configured to connect to the first irrigation port 246 and second irrigation port 252, and irrigation mechanism 30, e.g., a roller pump, is configured to provide irrigation fluid 62, such as, e.g., saline, to catheter assembly 240 and, more specifically, to a hypotube lumen 254, through irrigation tube 56.

The following items also relate to the invention:

In one form, the invention relates to a catheter assembly. The catheter assembly may comprise an outer sheath having a first end, a second end, and a frustoconical side wall portion located proximal to the second end. The outer sheath may have a sheath lumen that extends from the first end to the second end. The catheter assembly may comprise a hypotube ultrasonic transmission member disposed in the sheath lumen of the outer sheath. The hypotube ultrasonic transmission member may have a hypotube side wall, a proximal hypotube portion, a distal hypotube portion, and a tapered intermediate portion. The proximal hypotube portion may be configured to be operatively coupled to an ultrasonic transducer. The proximal hypotube portion may have a first diameter, and the distal hypotube portion may have a second diameter that is less than the first diameter. The tapered intermediate portion may be configured to transition from the first diameter of the proximal hypotube portion to the second diameter of the distal hypotube portion. The tapered intermediate portion may be located proximate the frustoconical side wall portion of the outer sheath.

In the embodiment of the previous paragraph, the catheter assembly may comprise a rapid exchange port formed in the hypotube side wall of the distal hypotube portion. The distal hypotube portion may be made from a magnetic material. A magnetic guide wire may be magnetically coupled to the distal hypotube portion, and the magnetic guide wire may be configured to extend through the rapid exchange port.

In some embodiments, the catheter assembly may also comprise a rapid exchange port formed in the hypotube side wall. The rapid exchange port may be configured for a guide wire to be extended therethrough.

In another form, the invention relates to an ultrasonic catheter system that may comprise an ultrasonic transducer, an outer sheath, and a hypotube ultrasonic transmission member. The outer sheath may have a first end, a second end, and a frustoconical side wall portion located proximal to the second end. The outer sheath may have a sheath lumen that extends from the first end to the second end. The hypotube ultrasonic transmission member may be disposed in the sheath lumen of the outer sheath. The hypotube ultrasonic transmission member may have a hypotube side wall, a proximal hypotube portion, a distal hypotube portion, and a tapered intermediate portion. The proximal hypotube portion may be operatively coupled to the ultrasonic transducer. The proximal hypotube portion may have a first diameter, and the distal hypotube portion has a second diameter that is less than the first diameter of the proximal hypotube portion. The tapered intermediate portion may be configured to transition from the first diameter of the proximal hypotube portion to the second diameter of the distal hypotube portion. The tapered intermediate portion may be located proximate the frustoconical side wall portion of the outer sheath.

In the embodiment of the previous paragraph, a first thickness of the hypotube side wall at the distal hypotube portion may be less than a second thickness of the hypotube side wall at the proximal hypotube portion.

In some embodiments, the hypotube ultrasonic transmission member has an exterior surface. The ultrasonic catheter system may comprise a guide wire tube connected directly to the exterior surface of the hypotube ultrasonic transmission member.

In some embodiments, the ultrasonic catheter system may comprise a rapid exchange port formed in the hypotube side wall of the distal hypotube portion. The distal hypotube portion may be made from a magnetic material. A magnetic guide wire may be magnetically coupled to the distal hypotube portion. The magnetic guide wire extends through the rapid exchange port.

In another form, the invention relates to an ultrasonic catheter system that may comprise an ultrasonic transducer configured to produce vibrational energy and a catheter assembly. The catheter assembly may comprise an outer sheath having a sheath lumen and a hypotube ultrasonic transmission member disposed in the sheath lumen of the outer sheath. The outer sheath may have a first end, a second end, and a frustoconical side wall portion located proximal to the second end. The sheath lumen may extend from the first end to the second end. The hypotube ultrasonic transmission member may include a hypotube side wall, a proximal hypotube portion, a distal hypotube portion, and a tapered intermediate portion. The proximal hypotube portion may be operatively coupled to the ultrasonic transducer. The proximal hypotube portion may have a first diameter. The distal hypotube portion may have a second diameter that may be less than the first diameter. The tapered intermediate portion may be configured to transition from the first diameter of the proximal hypotube portion to the second diameter of the distal hypotube portion. The tapered intermediate portion may be located proximate the frustoconical side wall portion of the outer sheath. The distal hypotube portion may be configured for longitudinal, transverse, or longitudinal and transverse displacement in accordance with the vibrational energy.

In the embodiment of the previous paragraph, the ultrasonic catheter system may comprise a first thickness of the hypotube side wall measured at the distal hypotube portion, and a second thickness of the hypotube side wall measured at the proximal hypotube portion. The first thickness is less than the second thickness.

In some embodiments, the distal hypotube portion may be configured to convert the vibrational energy received from the ultrasonic transducer into cavitation bubbles.

In some embodiments, the ultrasonic transducer may include a center lumen configured to allow a guide wire to be guided therethrough.

In the embodiment of the previous paragraph, the ultrasonic catheter assembly may comprise a roller pump that is configured to provide saline irrigation to the catheter assembly through the center lumen of the ultrasonic transducer.

In some embodiments, the ultrasonic catheter system may comprise a roller pump and an irrigation tube. The irrigation tube may be coupled to the roller pump. The outer sheath may have a sheath side wall and a first irrigation port may extend through the sheath side wall. The hypotube ultrasonic transmission member may have a second irrigation port extending through the hypotube side wall. The irrigation tube may be configured to connect to the first irrigation port and second irrigation port. The roller pump may be configured to provide saline irrigation to the catheter assembly through the irrigation tube.

In some embodiments, the outer sheath may have a sheath side wall and a first port extending through the sheath side wall. The hypotube ultrasonic transmission member may have a second port extending through the hypotube side wall. The ultrasonic catheter system may comprise a guide wire having a guide wire first end and a guide wire second end. The guide wire may be configured to extend through the first port and the second port. The guide wire second end is distal of the distal hypotube portion.

In some embodiments, the ultrasonic catheter system may comprise a rapid exchange port extending through the hypotube side wall. The rapid exchange port is configured for a guide wire to be extended therethrough.

In some embodiments, the outer sheath has an exterior surface. The ultrasonic catheter system may further comprise a guide wire lumen formed in part with the exterior surface of the outer sheath. The guide wire lumen may be connected to the second end of the outer sheath.

In some embodiments, the hypotube ultrasonic transmission member has an exterior surface. The ultrasonic catheter system may further comprise a guide wire tube that is connected directly to the exterior surface of the hypotube ultrasonic transmission member.

In some embodiments, the distal hypotube portion is made from a magnetic material. In these embodiments, the ultrasonic catheter system may comprise a magnetic guide wire that is magnetically coupled to the distal hypotube portion.

In the embodiment of the previous paragraph, the magnetic guide wire may have a surface coating of Teflon or silicone to reduce the friction between the hypotube ultrasonic transmission member and the magnetic guide wire.

As used herein, the term "coupled", and its derivatives, is intended to embrace any operationally functional connection, i.e., a direct connection or an indirect connection.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A catheter assembly, comprising:

an outer sheath having a first end, a second end, and a frustoconical side wall portion located proximal to the second end, and having a sheath lumen that extends from the first end to the second end; and a hypotube ultrasonic transmission member disposed in the sheath lumen of the outer sheath, the hypotube ultrasonic transmission member having a hypotube side wall, a proximal hypotube portion, a distal hypotube portion, and a tapered intermediate portion, the proximal hypotube portion configured to be operatively coupled to an ultrasonic transducer, the proximal hypotube portion having a first diameter, the distal hypotube portion having a second diameter less than the first diameter, and the tapered intermediate portion configured to transition from the first diameter of the proximal hypotube portion to the second diameter of the distal hypotube portion, and wherein the tapered intermediate portion is located proximate the frustoconical side wall portion of the outer sheath; and a rapid exchange port formed in the hypotube side wall, wherein the rapid exchange port is configured for a guide wire to be extended therethrough.

2. The catheter assembly according to claim 1, further comprising a first thickness of the hypotube side wall measured at the distal hypotube portion; and a second thickness of the hypotube side wall measured at the proximal hypotube portion, wherein the first thickness is less than the second thickness.

3. The catheter assembly according to claim 1, wherein the distal hypotube portion is made from a magnetic material; and a magnetic guide wire is magnetically coupled to the distal hypotube portion, the magnetic guide wire configured to extend through the rapid exchange port.

4. An ultrasonic catheter system, comprising:

an ultrasonic transducer;

an outer sheath having a first end, a second end, and a frustoconical side wall portion located proximal to the second end, and having a sheath lumen that extends from the first end to the second end;

a hypotube ultrasonic transmission member disposed in the sheath lumen of the outer sheath, the hypotube ultrasonic transmission member having an exterior surface, a hypotube side wall, a proximal hypotube portion, a distal hypotube portion, and a tapered intermediate portion, the proximal hypotube portion being operatively coupled to the ultrasonic transducer, the proximal hypotube portion having a constant first diameter along the proximal hypotube portion, the distal hypotube portion having a constant second diameter along the distal hypotube portion that is less than the constant first diameter, and the tapered intermediate portion configured to transition from the constant first diameter of the proximal hypotube portion to the constant second diameter of the distal hypotube portion, and wherein the tapered intermediate portion is located proximate the frustoconical side wall portion of the outer sheath; and a guide wire tube connected directly to the exterior surface of the hypotube ultrasonic transmission member.

5. The ultrasonic catheter system according to claim 4, wherein a first thickness of the hypotube side wall at the distal hypotube portion is less than a second thickness of the hypotube side wall at the proximal hypotube portion.

6. The ultrasonic catheter system according to claim 4, further comprising a rapid exchange port formed in the hypotube side wall of the distal hypotube portion, wherein the distal hypotube portion is made from a magnetic material; and a magnetic guide wire is magnetically coupled to the distal hypotube portion, the magnetic guide wire extends through the rapid exchange port.

7. The ultrasonic catheter system according to claim 4, wherein the proximal hypotube portion and the tapered intermediate portion are disposed within the outer sheath and the distal hypotube portion extends out of the second end of the outer sheath.

8. An ultrasonic catheter system, comprising:

an ultrasonic transducer configured to produce vibrational energy;

a catheter assembly comprising:

an outer sheath having a first end, a second end, and a frustoconical side wall portion located proximal to the second end, and having a sheath lumen that extends from the first end to the second end;

a hypotube ultrasonic transmission member disposed in the sheath lumen of the outer sheath, the hypotube ultrasonic transmission member having an exterior surface, a hypotube side wall, a proximal hypotube portion, a distal hypotube portion, and a tapered intermediate portion, the proximal hypotube portion being operatively coupled to the ultrasonic transducer, the proximal hypotube portion having a first diameter, the distal hypotube portion having a second diameter less than the first diameter, and the tapered intermediate portion configured to transition from the first diameter of the proximal hypotube portion to the second diameter of the distal hypotube portion, and wherein the tapered intermediate portion is located proximate the frustoconical side wall portion of the outer sheath; and a guide wire tube connected directly to the exterior surface of the hypotube ultrasonic transmission member, wherein the distal hypotube portion is configured for longitudinal, transverse, or longitudinal and transverse displacement in accordance with the vibrational energy, and wherein the hypotube ultrasonic transmission member includes a plurality of holes through the hypotube side wall at the distal hypotube portion to convert the vibrational energy received from the ultrasonic transducer into cavitation bubbles.

9. The ultrasonic catheter system according to claim 8, further comprising a first thickness of the hypotube side wall measured at the distal hypotube portion; and a second thickness of the hypotube side wall measured at the proximal hypotube portion, wherein the first thickness is less than the second thickness.

10. The ultrasonic catheter system according to claim 8, wherein the ultrasonic transducer has a center lumen configured to allow a guide wire to be guided therethrough.

11. The ultrasonic catheter system according to claim 10, further comprising a roller pump configured to provide saline irrigation to the catheter assembly through the center lumen of the ultrasonic transducer.

12. The ultrasonic catheter system according to claim 8, further comprising:

a roller pump;

an irrigation tube coupled to the roller pump;

the outer sheath having a sheath side wall and a first irrigation port extending through the sheath side wall; and the hypotube ultrasonic transmission member having a second irrigation port extending through the hypotube side wall, wherein the irrigation tube is configured to connect to the first irrigation port and second irrigation port, the roller pump is configured to provide saline irrigation to the catheter assembly through the irrigation tube.

13. The ultrasonic catheter system according to claim 8, further comprising:

the outer sheath having a sheath side wall and a first port extending through the sheath side wall;

the hypotube ultrasonic transmission member having a second port extending through the hypotube side wall; and a guide wire having a guide wire first end and a guide wire second end, the guide wire configured to extend through the first port and the second port, the guide wire second end is distal of the distal hypotube portion.

14. The ultrasonic catheter system according to claim 8, further comprising a rapid exchange port extending through the hypotube side wall, wherein the rapid exchange port is configured for a guide wire to be extended therethrough.

15. The ultrasonic catheter system according to claim 8, further comprising the outer sheath having an exterior surface; a guide wire lumen formed in part with the exterior surface of the outer sheath, wherein the guide wire lumen is connected to the second end of the outer sheath.

16. The ultrasonic catheter system according to claim 8, further comprising a magnetic guide wire is magnetically coupled to the distal hypotube portion, wherein the distal hypotube portion is made from a magnetic material.

17. The ultrasonic catheter system according to claim 16, further comprising the magnetic guide wire having a surface coating of Teflon or silicone to reduce the friction between the hypotube ultrasonic transmission member and the magnetic guide wire.

18. The ultrasonic catheter system according to claim 8, further comprising a guide wire disposed in the distal hypotube portion.

* * * * *